United States Patent
Hou et al.

(10) Patent No.: US 9,789,080 B2
(45) Date of Patent: Oct. 17, 2017

(54) OPHTHALMIC FORMULATIONS OF MYCOPHENOLIC ACID

(71) Applicant: INSITE VISION INCORPORATED, Alameda, CA (US)

(72) Inventors: Sui Yuen Eddie Hou, Alameda, CA (US); Lyle M. Bowman, Alameda, CA (US); Tang Nguyen, Alameda, CA (US); Gholam Peyman, Sun City, AZ (US)

(73) Assignees: Insite Vision Incorporated, Alameda, CA (US); Gholam Peyman, Sun City, AZ (US)

( * ) Notice: Subject to any disclaimer, the term of this patent is extended or adjusted under 35 U.S.C. 154(b) by 0 days.

(21) Appl. No.: 14/846,446

(22) Filed: Sep. 4, 2015

(65) Prior Publication Data

US 2017/0065552 A1   Mar. 9, 2017

(51) Int. Cl.
| | | |
|---|---|---|
| A01N 43/08 | (2006.01) | |
| A61K 31/34 | (2006.01) | |
| A61K 31/343 | (2006.01) | |
| A61K 9/00 | (2006.01) | |
| A61K 9/08 | (2006.01) | |
| A61K 31/365 | (2006.01) | |

(52) U.S. Cl.
CPC .......... *A61K 31/343* (2013.01); *A61K 9/0048* (2013.01); *A61K 9/08* (2013.01); *A61K 31/365* (2013.01)

(58) Field of Classification Search
USPC ........................................................ 514/470
See application file for complete search history.

(56) References Cited

U.S. PATENT DOCUMENTS

| | | | | |
|---|---|---|---|---|
| 5,497,910 A | * | 3/1996 | Meadows .......... | B65D 83/0055 222/209 |
| 7,083,803 B2 | | 8/2006 | Peyman | |
| 7,087,237 B2 | | 8/2006 | Peyman | |
| 2005/0245497 A1 | * | 11/2005 | Penfold ............... | A61K 31/573 514/179 |
| 2010/0010082 A1 | * | 1/2010 | Chong ................. | A61K 31/365 514/470 |

FOREIGN PATENT DOCUMENTS

| | | |
|---|---|---|
| WO | 2004/087174 A1 | 10/2004 |
| WO | 2005/030205 A1 | 4/2005 |
| WO | WO 2005/030205 * | 4/2005 |

OTHER PUBLICATIONS

Merck Index 14th Ed., 2006, monograph No. 6327, p. 1094.
International Search Report and Written Opinion dated Nov. 2, 2016, issued in International Application No. PCT/US2016/048125.

\* cited by examiner

*Primary Examiner* — Marcos Sznaidman
(74) *Attorney, Agent, or Firm* — McDermott Will & Emery LLP

(57) ABSTRACT

Ophthalmic formulations including mycophenolic acid or salt thereof in an aqueous medium having a reduced level of dissolved oxygen and processes for making such formulations and using such formulations are disclosed.

14 Claims, No Drawings

OPHTHALMIC FORMULATIONS OF MYCOPHENOLIC ACID

TECHNICAL FIELD

The present disclosure relates to ophthalmic formulations including mycophenolic acid and salts thereof with a reduced level of dissolved oxygen and the preparation and use of such formulations.

BACKGROUND

Mycophenolic acid is an immunosuppressant and used to prevent rejection in organ transplantation. It has also been used in ocular solutions for treating ocular inflammation at a surgical site, inhibiting cell migration and cell proliferation, inhibiting growth of new blood vessels at a site of an ocular tumor, and reducing growth of bacteria and fungi. See U.S. Pat. Nos. 7,083,803 and 7,087,237 and International Patent Publication No. WO2005030205.

However, mycophenolic acid is difficult to formulate as an ophthalmic solution; it is almost insoluble in cold water. See Merck Index 14$^{th}$ Ed. 2006, monograph no. 6327. Accordingly, a need exists to improve the preparation of ophthalmic formulations of mycophenolic acid.

SUMMARY OF THE DISCLOSURE

Advantages of the present disclosure include ophthalmic formulations including mycophenolic acid or salt thereof with improved stability and processes for making such formulations and using such formulations.

These and other advantages are satisfied, at least in part, by an ophthalmic formulation comprising mycophenolic acid or salt thereof as an active ingredient in an aqueous medium with a reduced level of dissolved oxygen relative to saturation level. In some embodiments, the ophthalmic formulation has a shelf-life in which at least 90% or 95% of an initial amount of the mycophenolic acid or salt thereof as an active ingredient remains in the ophthalmic formulation after a period of at least 12 or 18 months from an initial preparation of the ophthalmic formulation and preferably after a period of at least 24 months from an initial preparation of the ophthalmic formulation.

Another aspect of the present disclosure includes an ophthalmic formulation comprising mycophenolic acid or salt thereof as an active ingredient and an antioxidant, e.g., an alkali thiosulfate, in an aqueous medium with a reduced level of dissolved oxygen relative to saturation level.

Another aspect of the present disclosure includes an ophthalmic formulation comprising mycophenolic acid or salt thereof as an active ingredient in an aqueous medium with a dissolved oxygen level of less than 3 ppm, e.g., less than 2.0 ppm.

Another aspect of the present disclosure includes an ophthalmic formulation comprising mycophenolic acid or salt thereof as an active ingredient in an aqueous medium with a reduced level of dissolved oxygen relative to saturation level packaged in an opaque container or pouch including a metal foil for reducing oxygen permeability through the container or pouch.

Embodiments of the present disclosure include one or more of the following features individually or combined. For example, the aqueous medium can have an oxygen level of less than 1.0 ppm such as no more than 0.5 ppm. In some embodiments, the ophthalmic formulation can include an alkali thiosulfate, e.g., sodium thiosulfate. In other embodiments, the ophthalmic formulation can include one or more additional ingredients such as an ophthalmically acceptable vehicle, viscosity modifier, buffer, osmolality adjusting agent, pH adjusting agent, antioxidant, chelating agent, preservative, and/or wetting agent. In various embodiments, the ophthalmically acceptable vehicle can be included in an amount to adjust a viscosity of the ophthalmic formulation to between about 1,000 cps to about 5,000 cps. In still further embodiments, the ophthalmic formulation can be packaged in an opaque container or pouch including a metal foil for reducing oxygen permeability through the container or pouch.

Another aspect of the present disclosure includes methods of treating a subject with the ophthalmic formulations of the present disclosure. A method includes administering to an eye of a subject in need thereof the ophthalmic formulation of the present disclosure.

Embodiments of the present disclosure include one or more of the following features individually or combined. For example, the methods can include administering the ophthalmic formulation into the eye of the subject by injecting the formulation. In some embodiments, the methods include treating a subject having an immune system disorder. In various embodiments, the methods include treating a subject having sjogren's syndrome, rheumatoid arthritis, or lupus, for example, or treating dry eye.

Another aspect of the present disclosure includes methods of manufacturing the ophthalmic formulations of the present disclosure. The methods include either (i) combining mycophenolic acid or salt thereof as an active ingredient with an aqueous medium having a reduced level of dissolved oxygen relative to saturation level or (ii) combining mycophenolic acid or salt thereof as an active ingredient with an aqueous medium followed by reducing a level of dissolved oxygen relative to saturation level in the aqueous medium to manufacture the ophthalmic formulation.

Embodiments of the present disclosure include one or more of the following features individually or combined. For example, the methods can include reducing the dissolved oxygen level to less than 3.0 ppm, e.g., less than 2 ppm or less and 1.0 ppm. In various embodiments, the methods can include adding one or more additional ingredients to the aqueous medium while maintaining a reduced level of dissolved oxygen relative to saturation level in the aqueous medium. In some embodiments, the methods include adding an alkali thiosulfate to the aqueous medium or adjusting the pH of the aqueous medium to greater than 7.0. In other embodiments, the methods can include combining mycophenolic acid or salt thereof with the aqueous medium without exposing the mycophenolic acid or salt thereof to a substantial amount of light. In still further embodiments, the methods include adding an ophthalmically acceptable vehicle to the ophthalmic formulation, e.g., polycarbophil and optionally chitosan, and/or adding an ophthalmically acceptable vehicle in an amount to adjust a viscosity of the ophthalmic formulation to between about 1,000 cps to 5,000 cps. In various embodiments, the methods include packaging the ophthalmic formulation in an opaque container or pouch which includes a metal foil for reducing oxygen permeability through the container or pouch.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the description is to be regarded as illustrative in nature, and not as restrictive.

DETAILED DESCRIPTION OF THE DISCLOSURE

The present disclosure is directed to ophthalmic formulations of mycophenolic acid and salts thereof, e.g., sodium mycophenolate. It was found that ophthalmic formulations including mycophenolic acid and salts thereof as an active ingredient therein have decrease activity of the active ingredient over time. It was further found that loss of activity of such formulations occur in the presence of oxygen and/or when exposed to light. Under such conditions, the active ingredient in an ophthalmic formulation can be significantly reduced over a period of 3-6 months.

In practicing an aspect of the present disclosure, an ophthalmic formulation including mycophenolic acid or salt thereof can be manufactured by preparing the formulation with a reduced level of oxygen dissolved in the formulation. Typically, ophthalmic formulations include an aqueous medium that is principally composed of water and optionally other ophthalmically compatible ingredients. Saturated water can contain approximately 9 ppm of oxygen dissolved therein at room temperature (i.e., 20° C.) under one atmosphere and physiological pH.

It was found that ophthalmic formulations including mycophenolic acid or salt thereof as an active ingredient in an aqueous medium with a reduced level of dissolved oxygen relative to saturation level were more stable than formulations with aqueous media having saturated levels of dissolved oxygen. The improved stability allows for the manufacture of ophthalmic formulations containing mycophenolic acid or salt thereof with a significantly improved shelf-life, e.g., formulations having a shelf-life of over 12 months.

Dissolved oxygen can be removed from the ophthalmic formulation in at least two ways. These include: (i) first preparing an ophthalmic formulation comprising mycophenolic acid or salt thereof followed by removing dissolved oxygen or (ii) first removing oxygen from the aqueous medium followed by combining mycophenolic acid or salt thereof with the aqueous medium having a reduced level of dissolved oxygen. It was found that second process produced more stable ophthalmic formulations. That is, combining mycophenolic acid or salt thereof as an active ingredient with an aqueous medium with a reduced level of dissolved oxygen relative to saturation level (i.e., a deoxygenated aqueous medium) formed a more stable formulation than by first forming the formulation followed by removing dissolved oxygen therefrom.

The removal of dissolved oxygen from the formulation can be carried out by any conventional means including applying a vacuum to the medium and/or inert atmosphere distillation, freeze-thaw degassing, use of degassing filters, etc. A convenient technique for removing dissolved oxygen includes passing an inert gas through the medium, i.e., sparging, to remove dissolved oxygen from the formulation or aqueous medium. Inert gases that can be used in the present disclosure include those that do not substantially degrade mycophenolic acid or salt thereof such as nitrogen, argon, helium, etc.

It is believed that dissolved oxygen in an ophthalmic formulation including mycophenolic acid or salt thereof adversely decreases the availability of the active ingredient in the formulation. It may oxidize and/or decompose the mycophenolic acid or salt thereof. It is further believed that by removing the dissolved oxygen from the formulation, the formulation is more stable and has a significantly longer shelf-life.

In an aspect of the present disclosure, the reduced level of dissolved oxygen is preferably sufficient to establish a shelf-life sufficient for commercial manufacture and distribution of the ophthalmic formulation such as a shelf-life of least 12 months, e.g., at least 18 months, 24 months, or more. In an embodiment, ophthalmic formulations of the present disclosure have a shelf-life characteristic in which at least 90% or 95% of an initial amount of the mycophenolic acid or salt thereof as an active ingredient remains in the ophthalmic formulation after a period of at least 12 or 18 months from an initial preparation of the ophthalmic formulation and preferably after a period of at least 24 months from an initial preparation of the ophthalmic formulation. The stability or shelf-life characteristic of a formulation can be determined by various processes known in the art including accelerating aging studies and determining the amount of mycophenolic acid or salt thereof remaining in the formulation can be assessed by an HPLC assay having a ±2% accuracy or equivalent.

In an embodiment of the present disclosure, an ophthalmic formulation including mycophenolic acid or salt thereof as an active ingredient can be prepared by reducing the level of oxygen dissolved in the medium or formulation to less than 3.0 ppm, e.g., less than 2.0 ppm and preferably less than 1.0 ppm such as no more than 0.5 ppm. The dissolved oxygen level of the formulation can be determined with VWR SympHony, model SP70D, meter or an equivalent meter. Preferably the oxygen meter should have a relative accuracy of about 0.2 mg/L. The measurement is taken at room temperature (i.e., 20° C.) under one atmosphere and physiological pH.

In addition, mycophenolic acid or salt thereof can be combined with an aqueous medium, e.g., a deoxygenated aqueous medium, under conditions that do not expose the mycophenolic acid or salt thereof to a substantial amount of light. For example, the combination of mycophenolic acid or salt thereof with an aqueous medium and/or other ingredient can be carried out in an opaque container and any transfers of the aqueous formulation can be carried out through opaque tubing into other opaque containers. It is further preferably to handle any deoxygenated formulations of mycophenolic acid or salt thereof in an inert atmosphere so as to maintain the reduced level of oxygen therein.

It was further found that adjusting the pH of an aqueous medium or formulation of mycophenolic acid or salt thereof to a pH of greater than 7.0 facilitates dissolution of the active ingredient. In an embodiment of the present disclosure, the pH of an ophthalmic formulation including mycophenolic acid or salt thereof in an aqueous medium with a reduced level of oxygen dissolved in the ophthalmic formulation can be adjusted to a pH of greater than 7.0, e.g., at least about 7.4, such as at least about 7.8. In an embodiment, the ophthalmic formulation of the present disclosure has a pH in a range of 7.4 to 7.8 with a specification of ±0.3 pH units.

The ophthalmic formulation of the present disclosure and processes for preparing such formulations can include adding one or more additional ingredients. Such additional ingredients can include, for example, one or more ophthalmically acceptable vehicles, viscosity modifiers, buffers, osmolality adjusting agents, pH adjusting agents, antioxidants, preservatives, wetting agents, etc. It is preferably that any additional ingredients added to the ophthalmic formulation of the present disclosure be added so as not to introduce any significant amount of oxygen to the formulation. For example, the one or more additional ingredients can be prepared in a deoxygenated aqueous medium and then added to the formulation. The one or more additional ingredients can be prepared in a deoxygenated aqueous medium, e.g., distilled water or water for injection, by preparing a formulation with the ingredient followed by reducing the level of dissolved oxygen or by adding the ingredient to a deoxygenated aqueous medium. By this method the reduced level of dissolved oxygen is maintained in the aqueous medium during addition of additional ingredients thereto.

Ophthalmic formulations of the present disclosure and processes for preparing such formulations can include adding one or more antioxidants. Such antioxidants include alkali sulfites such as sodium sulfite, sodium bisulfite, sodium metabisulfite, sodium or potassium thiosulfate, sulfur dioxide, ascorbic acid, isoascorbic acid, thioglycerol, thioglycolic acid, cysteine hydrochloride, acetylcycsteine. It was found that an alkali thiosulfate, e.g., sodium thiosulfate, provided ophthalmic formulation of the present disclosure with enhanced stability over periods of over a year without significant loss of activity of mycophenolic acid. In contrast, sodium bisulfite reacted with the formulation to form a yellow precipitate and did not provide the ophthalmic formulation of the present disclosure with any apparent benefit in stability of the mycophenolic acid.

Chelating agents can also be added to the ophthalmic formulations of the present disclosure. Such chelating agents include, for example, EDTA, citric acid, etc.

Ophthalmic formulations of the present disclosure and processes for preparing such formulations can include adding one or more osmolality-adjusting compounds. Such compounds include various non-ionic osmolality-adjusting compounds such as polyhydric alcohols, including for example, glycerol, mannitol, sorbitol, or propylene glycol and ionic salts such as sodium or potassium chloride.

In some embodiments, the osmolality of the formulation can be adjusted to from about 10 mOsm/kg to about 400 mOsm/kg, and in other embodiments, from about 100 to about 300 mOsm/kg, using appropriate amounts of physiologically and ophthalmologically acceptable salts. Sodium chloride can be used as an osmolality adjusting agent to adjust the osmolality of the aqueous suspension to approximate that of physiologic fluid. The amounts of sodium chloride ranging from about 0.01% to about 1% by weight, and in other embodiments from about 0.05% to about 0.45% by weight, based on the total weight of the aqueous suspension, will give osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfite and the like, e.g., potassium chloride, sodium thiosulfate, sodium bisulfite, ammonium sulfate, and the like can also be used in addition to or instead of sodium chloride to achieve osmolalities within the above-stated ranges.

Ophthalmic formulations of the present disclosure and processes for preparing such formulations can include adding one or more buffers or buffer systems to maintain and/or adjust the formulation to an acceptable pH. Buffer systems useful for the present disclosure include, but not limited to, acetate buffers, citrate buffers, phosphate buffers, borate buffers and mixtures thereof. Specific buffer components useful in the present disclosure include, but not limited to, citric acid/sodium citrate, boric acid, sodium borate, sodium phosphates, including mono, di- and tri-basic phosphates, such as sodium phosphate monobasic monohydrate and sodium phosphate dibasic heptahydrate, and mixtures thereof. It should be noted that any other suitable ophthalmically acceptable buffer components can be employed to maintain the pH of the ophthalmic formulation so that the ophthalmic formulation is provided with an acceptable pH, and the foregoing buffer components are merely exemplary examples of such buffer components.

Ophthalmic formulations of the present disclosure and processes for preparing such formulations can include adding one or more preservatives. Suitable preservatives include, for example, chlorobutanol, Polyquat, benzalkonium chloride, cetyl bromide, benzethonium chloride, cetyl pyridinium chloride, benzyl bromide, EDTA, phenylmercury nitrate, phenylmercury acetate, thimerosal, merthiolate, acetate and phenylmercury borate, chlorhexidine, polymyxin B sulphate, methyl and propyl parabens, phenylethyl alcohol, quaternary ammonium chloride, sodium benzoate, sodium proprionate, sorbic acid, and sodium perborate. In particular embodiments, the preservative includes benzalkonium chloride. It is preferred that the ophthalmic formulations of the present disclosure do not contain preservatives, being preservative free, or if one or more preservatives are present, they are present in very low concentrations.

In some embodiments, the preservative is present in a range from about 0.001 to about 0.02% by weight. The preservative can be present at about 0.001, 0.002, 0.003, 0.004, 0.005% and any amount in between these amounts. In an embodiment, an ophthalmic formulation is preservative free. As described below, the formulation can be filled into unit dose containers, over wrapped into foil laminate pouches, and filled with nitrogen in the headspace.

Ophthalmic formulations of the present disclosure and processes for preparing such formulations can include adding one or more wetting agents. Such wetting agents include, for example, Poloxamer 407, a triblock copolymer consisting of a central hydrophobic block of polypropylene glycol flanked by two hydrophilic blocks of polyethylene glycol. Other wetting agents that can be used include carboxymethylcellulose, hydroxypropyl methylcellulose, glycerin, mannitol, polyvinyl alcohol, Octoxynol 40 and hydroxyethylcellulose. Many of the polymeric wetting agents can also act as viscosity modifiers.

Ophthalmic formulations of the present disclosure and processes for preparing such formulations can include adding one or more ophthalmically acceptable vehicles. Such vehicles include, for example, at least one lightly cross-linked carboxy-containing polymer, e.g., a polycarbophil, Carbopol, or Noveon polymer. In certain embodiments, the vehicle can further include a second polymer, e.g., chitosan. The cross-linked carboxy-containing polymer can be included in the formulation in an amount from about 0.1% to about 6.5%, e.g., from about 0.5% to about 1.5%, by weight, based on the total weight of the formulation.

In some embodiments, chitosan having a molecular weight in a range from between about 50 kDa to about 100 kDa, including any weights in between, e.g., chitosan having a molecular weight in a range from between about 1,000 to about 3,000 kDa, and any weights in between, can be used as an ophthalmically acceptable vehicle. If present, the chitosan can be present in an amount ranging from between about 0.01% to about 0.5%.

The ophthalmic vehicle preferably has desirable rheological properties that are conducive to medicament delivery into the eye and provide corneal retention. The vehicle uses a combination of an anionic carboxy-containing polymer in conjunction with a substantially smaller amount of a second polymer, for example, a cationic polymer. The second polymer is included at a sufficient concentration such that the particles of the carboxy-containing polymer remain suspended without precipitation, yet when combined with the second polymer, the resulting vehicle has higher viscosity than the vehicle with the carboxy-containing polymer alone. The vehicle disclosed herein has the property that, when combined with tear fluid, its viscosity increases due to the higher pH of tear fluid, or a decrease in pH if formulated higher than neutral pH. The resultant viscosity provides a means by which to increase the efficiency of medicament delivery by increased corneal retention.

In some embodiments, the ophthalmically acceptable vehicle includes an aqueous suspension containing from about 0.1% to about 6.5%, e.g., from about 0.5% to about 1.5%, by weight, based on the total weight of the suspension, of a carboxyl-containing polymer prepared by polymerizing one or more carboxyl-containing monoethylenically unsaturated monomers and less than about 5% by weight of a crosslinking agent. The weight percentages of monomers are based on the total weight of monomers polymerized. The carboxyl-containing polymer has an average particle size of not more than about 50 μm in equivalent spherical diameter and is lightly cross-linked.

The vehicle can further include a second polymer, such as a chitosan, added in sufficient amount to increase the vehicle viscosity without the loss of polymer precipitating, while still allowing the vehicle to be administered to the eye in drop form to increase formulation retention in the eye.

Additional ophthalmically acceptable vehicles include, without limitation, hydroxyproplymethyl cellulose (HPMC), hydroxypropyl cellulose (HPC), methyl cellulose (MC), hydroxyethyl cellulose (HEC), polyacrylic acid (PAA), polyvinyl alcohol, carbomers, sodium hyaluronate, cyclodextrins, polygalacturonic acid, polyitaconic acid, xyloglucan, xanthan gum, gellan gum, polysaacride gums, polyorthoesters, celluloseacetophthalate, poloxamer 407, polyethyleneimine, and polyethylene oxide. When used as a topical formulation, the viscosity of the ophthalmic formulation of the present disclosure can be adjusted to viscosities ranging from about 1,000 centipoise (cps) to about 30,000 cps, and in other embodiments from about 1,000 to about 5,000 cps, e.g., between about 1,000 to about 2, 000 cps, as measured at room temperature (about 25° C.) using a Brookfield Digital LVT Viscometer equipped with a number 25 spindle and a 13R small sample adapter at 12 rpm. The viscosity of the formulation can be adjusted by including an appropriate amount of an ophthalmically acceptable vehicle.

The ophthalmic formulation of the present disclosure can include active agents in addition to mycophenolic acid or salts thereof. For example, the ophthalmic formulation of the present disclosure can include can include antibiotics, non-steroidal anti-inflammatory drugs (NSAID), and steroids, such as dexamethasone, its salts, esters, etc.

Ophthalmic formulations of the present disclosure and processes for preparing such formulations can include packaging the ophthalmic formulation in an opaque container to prevent exposure of the formulation to a substantial amount of light and/or with an inert atmosphere. The process can include purging the empty container with an inert gas, e.g., $N_2$, before filling and filling the container with the ophthalmic formulation. The container can be opaque when filled and can be wrapped with a label or metal foil to prevent the formulation from being exposed to substantial light. A container including a metal foil also advantageously reduces oxygen permeability from the atmosphere through the container. The containers can be of the type for a single dose administration; e.g., in a bottle, jar, ampoule, tube, syringe, envelope, container, unit dose container or vial or the container can be of the type that is capable of holding multiple doses; e.g., in resealable glass or plastic eyedropper bottles, etc. The bottles whether multi-dose or single dose can be packaged in a laminate pouch including a metal foil to minimize exposer to oxygen from the atmosphere. Further, the pouch can be filled with an inert atmosphere to further reduce oxygen exposure over long-term storage to improve stability.

Another aspect of the present disclosure includes an ophthalmic formulation including mycophenolic acid or salt thereof and a deoxygenated aqueous medium. In some embodiments, the deoxygenated aqueous medium has an oxygen content of less than 2 ppm and preferably less than about 1 ppm. The oxygen level of the formulation can be determined with an oxygen meter such as a VWR Symphony, model SP70D meter or an equivalent meter. The ophthalmic formulation of the present disclosure can have a pH of greater than 7.2, e.g., at least about 7.4, or in a range of about pH 7.4 to about 7.8. The ophthalmic formulation of the present disclosure can also optionally include any of the ingredients described above, including various embodiments thereof. Such additional ingredients can include, for example, one or more ophthalmically acceptable vehicles, viscosity modifiers, buffers, osmolality adjusting agents, pH adjusting agents, antioxidants, preservatives, wetting agents, etc.

Another aspect of the present disclosure includes methods for treating subjects with an ophthalmic formulation including mycophenolic acid or salt thereof and a deoxygenated aqueous medium. Such methods include administering to an eye of a subject in need of treatment the ophthalmic formulation of the present disclosure. The ophthalmic formulation of the present disclosure can be administered topically or invasively, e.g., by injecting the formulation into an eye of a subject in need of such intervention. The ophthalmic formulation of the present disclosure can be used to treat a subject having an immune system disorder such as sjogren's syndrome, rheumatoid arthritis, lupus, etc. and/or the symptom of dry eye.

Other indications that can be treated by ophthalmic formulations of the present disclosure include allergic conjunctivitis, corneal transplantation, inflammation, and uveitis

EXAMPLES

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

General Ophthalmic Formulation with Polycarbophil and Chitosan

All water used is sparged with nitrogen prior to use. All headspaces of mixing vessels are filled with nitrogen. All solution transfers are conducted under nitrogen.

In a first step (polycarbophil formulation), ethylenediaminetetraacetic acid (EDTA), sodium chloride (both dissolved in deoxygenated water) and polycarbophil are mixed for 30 minutes using an overhead mixer. The solution is then transferred to a stainless steel pressure can. The solution is transferred using pressure through a 100 mesh screen into the 12 L vessel. This solution is sterilized within the tank at 121.1° C. for 30 minutes.

In the second step (chitosan formulation), chitosan is dispersed in deoxygenated water and hydrochloric acid is added to achieve dissolution of the chitosan. This is then added aseptically to the vessel through a 0.2 um filter. Sodium hydroxide solution is then added aseptically through a 0.2 μm filter to the vessel. The stainless steel pressure can and transfer line are then rinsed with house DI water and added aseptically to the vessel.

In a third step (Active Ingredient), octoxynol 40 is dissolved in deoxygenated water, followed by mycophenolic acid with the aid of sodium hydroxide. After mycophenolic acid is completely dissolved, this solution is transferred aseptically to the solution in the 12 L vessel followed by a deoxygenated DI water rinse. Sodium hydroxide is then added aseptically to the vessel followed by a deoxygenated DI water rinse.

In a fourth step (Preservative/Osmotic Agent), benzalkonium chloride and mannitol are dissolved in water and added aseptically to the vessel followed by a deoxygenated DI water rinse.

In a fifth step (Antioxidant), sodium thiosulfate is dissolved in deoxygenated water and then added aseptically to the vessel. Sodium hydroxide is then added aseptically to the vessel to achieve the target pH of 7.8. The stainless steel pressure can and filter are then rinsed with deoxygenated DI water and the rinsate is added aseptically to the solution in the 12 L vessel. The rinse volume is determined by targeting a final batch volume of 12 liters.

12 Kg Batch Ophthalmic Formulation

All water used is sparged with nitrogen prior to use in the process. All headspaces of vessels are filled with nitrogen and all solution transfers are conducted under nitrogen.

Solution 1 (Polycarbophil): In a suitable container, edetate disodium dehydrate is added to de-ionized water and mixed until dissolved. Sodium chloride is added and mixed until dissolved. With the vessel under a nitrogen blanket, polycarbophil is added and mixed to form a dispersion. The polycarbophil dispersion is transferred into a compounding vessel through a 100-mesh screen. The polycarbophil dispersion is heat sterilized at 121° C. for at least 25 minutes while maintained under constant mixing. The polycarbophil dispersion is cooled to below 30° C. under agitation before further processing.

Solution 2 (Chitosan): In a suitable container under nitrogen blanket, NaCl is added to de-ionized water and mixed until dissolved. An octoxynol 40 solution is added and mixed until a homogeneous solution is achieved. Chitopharm L is added and mixed until completely dispersed. 2N HCl is added and mixed until the chitosan is completely dissolved. The chitosan mixture is vacuum-filtered through a prefilter. The chitosan filtrate is then transferred to the compounding vessel containing the cooled polycarbophil dispersion through a sterilizing filter. 2N sodium hydroxide, NF is added to the polycarbophil-chitosan mixture in the compounding vessel via a sterilizing filter. Rinse with water.

Solution 3 (Active Ingredient): In a suitable container under nitrogen blanket octoxynol 40 in solution is added to de-ionized water and mixed until a homogenous. Mycophenolic acid is then added and mixed until uniformly dispersed. 2N NaOH is added to adjust the pH of the solution to 7.9 to completely dissolve the mycophenolic acid. This solution is transferred to the compounding vessel through the sterilizing filter using nitrogen pressure. Rinse with water. 2N NaOH is added to the compounding vessel through the sterilizing filter. Rinse with water.

Solution 4 (Preservative/Osmotic Agent): Benzalkonium chloride solution is added to de-ionized water in a suitable container under a nitrogen blanket. Mannitol is added and mixed until completely dissolved. This solution is transferred to the compounding vessel through the sterilizing filter and mixed. Rinse with water.

Solution 5 (Antioxidant): In a suitable container with de-ionized water under nitrogen blanket, sodium thiosulfate is added and mix until dissolved. This solution is transferred to the compounding vessel through the sterilizing filter and mixed. Rinse with water. 2N NaOH is added to the compounding vessel through the filter to adjust the pH of the batch to a pH of 7.8. De-ionized water is added to compounding vessel through the filter and mixed to achieve the batch size of 12 kg.

The relative weight percent concentrations of the ingredients for this example are provided in the table below.

| Ingredients | Concentration (w/w %) |
| --- | --- |
| EDTA (Disodium Edetate Dihydrate) | 0.1 |
| Sodium Chloride | 0.4 |
| Polycarbophil | 0.95 |
| Octoxynol 40 (70% Solution) | 0.02 |
| Chitopharm-L | 0.05 |
| Hydrochloric Acid 2N (chitosan dissolution) | 1.5 |
| Mycophenolic Acid | 0.5 |
| 2N NaOH (active dissolution @ pH 7.9) | q.s. to adjust pH to 7.9 |
| Benzalkonium Chloride (5% overage) | 0.00315 |
| Mannitol | 0.15 |
| Sodium thiosulfate | 0.3 |
| 2N NaOH (pH adjustment) | q.s. to adjust pH to 7.8 |
| Water | q.s. to 100% |

The stability of a sample of the batch described above was determined to have a shelf-life in which at least 95% of an initial amount of the mycophenolic acid or salt thereof as an active ingredient remains in the ophthalmic formulation after a period of at least 18 months.

Formulations of Mycophenolic Acid with Polycarbophil or Carboxymethyl Cellouse Viscosity Modifiers.

Tables 1A and 1B show representative formulations of mycophenolic acid with polycarbophil or carboxymethyl cellulose in weight percentages.

TABLE 1A

| | Formulation | | | | | | |
| --- | --- | --- | --- | --- | --- | --- | --- |
| Component | 1 % | 2 % | 3 % | 4 % | 5 % | 6 % | 7 % |
| Mycophenolic acid | 0.1 | 0.1 | 0.1 | 0.1 | 0.1 | 0.25 | 0.25 |
| Citric Acid | — | — | 0.2 | — | — | 0.2 | 0.2 |
| Sodium Citrate | — | — | 0.14 | — | — | 0.14 | 0.14 |
| Sodium Chloride | 0.45 | 0.45 | 0.6 | 0.45 | 0.45 | 0.45 | 0.45 |
| Mannitol | 1.0 | 1.0 | 1.0 | 1.0 | 1.0 | 1.0 | 1.0 |
| EDTA | 0.1 | 0.1 | 0.1 | 0.1 | 0.1 | 0.1 | 0.1 |
| Poloxamer 407 | — | 0.2 | — | — | — | — | 0.2 |
| Octoxynol 40 (70%) | 0.02 | — | 0.02 | 0.02 | 0.02 | 0.02 | — |
| Sodium Thiosulfate | 0.3 | 0.3 | — | 0.3 | 0.3 | — | — |
| Benzalkonium Chloride | 0.003 | — | 0.003 | 0.003 | 0.003 | 0.003 | — |
| Polycarbophil | 0.9 | 0.9 | — | 0.9 | — | — | — |
| Carboxymethyl Cellulose | — | — | 1.0 | — | 1.0 | 1.0 | 1.0 |
| Sodium Hydroxide | qs to 7.4 | qs to 7.4 | qs to 7.4 | qs to 7.4 | qs to 7.4 | qs to 7.4 | qs to 7.4 |

TABLE 1A-continued

| | Formulation | | | | | | |
|---|---|---|---|---|---|---|---|
| Component | 1 % | 2 % | 3 % | 4 % | 5 % | 6 % | 7 % |
| Water | qs to 100% | qs to 100% | qs to 100% | qs to 100% | qs to 100% | qs to 100% | qs to 100% |

TABLE 1B

| | Formulation | | | | | |
|---|---|---|---|---|---|---|
| Component | 8 % | 9 % | 10 % | 11 % | 12 % | 13 % |
| Mycophenolic acid | 0.25 | 0.25 | 0.5 | 0.5 | 0.5 | 0.5 |
| Citric Acid | 0.2 | 0.2 | 0.2 | — | — | 0.2 |
| Sodium Citrate | 0.14 | 0.14 | 0.14 | — | — | 0.14 |
| Sodium Chloride | 0.45 | 0.45 | 0.45 | 0.45 | 0.45 | 0.45 |
| Mannitol | 1.0 | 1.0 | 1.0 | 1.0 | 1.0 | 1.0 |
| EDTA | 0.1 | 0.1 | 0.1 | 0.1 | 0.1 | 0.1 |
| Poloxamer 407 | — | 0.2 | — | — | 0.2 | 0.2 |
| Octoxynol 40 (70%) | 0.02 | — | 0.02 | 0.02 | — | — |
| Sodium Thiosulfate | — | — | — | 0.3 | 0.3 | — |
| Benzalkonium Chloride | 0.003 | — | 0.003 | 0.003 | — | — |
| Polycarbophil | 0.9 | 0.9 | 0.9 | 0.9 | 0.9 | — |
| Carboxymethyl Cellouse | — | — | — | — | — | 1.0 |
| Sodium Hydroxide | qs to 7.4 | qs to 7.4 | qs to 7.8 | qs to 7.8 | qs to 7.8 | qs to 7.8 |
| Water | qs to 100% | qs to 100% | qs to 100% | qs to 100% | qs to 100% | qs to 100% |

The examples in Tables 1A and 1B can be prepared according to the following 4 representative examples.

Example 1

Prepare deoxygenated water having an oxygen content of less than 0.5 ppm for the formulation by degassing water, e.g., DI water, sterile water for injection, etc., with nitrogen or argon by bubbling the gas through the water until a reading of less than 0.5 ppm of $O_2$ is obtained using a dissolved oxygen meter, such as a VWR Symphony, model SP70D meter. Maintain the level of dissolved oxygen in the water during the formulation process at 0.5 or less ppm of $O_2$ by continuing to bubble inert gas through the solutions at all times including when adding the various ingredients.

Dissolve NaCl and EDTA in the deoxygenated water, and slowly disperse the polycarbophil into the salt solution by mixing with a propeller mixer until evenly dispersed. Place the solution in the appropriate vessel for the size of the batch and heat at 123° C. for a minimum of 30 minutes to sterilize and slowly cool to room temperature. Maintain sterility of the vessel and back fill with sterile filtered $N_2$ or Ar.

Dissolve mannitol, citrate buffer and benzalkonium chloride (BAC), if present, in the deoxygenated water and adjust the pH of the solution to 5.5 with 2N NaOH prepared form the deoxygenated water. Sterile filter this solution into the sterilized formulation using $N_2$. In an opaque vessel protecting from light using the deoxygenated water, dissolve mycophenolic acid, and octoxynol, and adjust the pH to 7.9 with 2N NaOH. Sterile filter this solution in the formulation while maintaining a $N_2$ headspace over the formulation. Adjust the pH of the formulation to 7.8 using 2N NaOH while maintaining the nitrogen headspace/sterility.

The formulation is then filled into multi-dose bottles which have been sterilized by Co-60 irradiation by purging the empty bottle with $N_2$ before filling and filling with the formulation leaving nitrogen headspace in the filled bottle. The bottle is then overwrapped with a foil laminate pouch by purging the pouch with nitrogen and heat sealing.

Example 2

Prepare deoxygenated water having an oxygen content of less than 0.5 ppm for the formulation by degassing water, e.g., DI water, sterile water for injection, etc., with nitrogen or argon by bubbling the gas through the water until a reading of less than 0.5 ppm of $O_2$ is obtained using a dissolved oxygen meter, such as a VWR Symphony, model SP70D meter. Maintain the level of dissolved oxygen in the water during the formulation process at 0.5 or less ppm of $O_2$ by continuing to bubble inert gas through the solutions at all times including when adding the various ingredients.

Dissolve the NaCl and EDTA in the deoxygenated water, and slowly disperse the polycarbophil into the salt solution by mixing with a propeller mixer until evenly dispersed. Place the solution in the appropriate vessel for the size of the batch and heat at 123° C. for a minimum of 30 minutes to sterilize and slowly cool to room temperature. Maintain sterility of the vessel and back fill with sterile filtered N2 or Ar.

Dissolve mannitol and citrate buffer in the deoxygenated water and adjust the pH of the solution to 5.5 with 2N NaOH prepared from the deoxygenated water. Sterile filter this solution into the sterilized formulation using $N_2$. In an opaque vessel protecting from light using the deoxygenated water, dissolve mycophenolic acid and poloxamer, and adjust the pH to 7.9 with 2N NaOH. Sterile filter this solution in the formulation while maintaining a $N_2$ headspace. Adjust the pH of the formulation to 7.8 using 2N NaOH while maintaining the nitrogen headspace/sterility.

The formulation is then filled into $N_2$ purged unit dose containers produced on a blow fill seal line. The unit dose containers are then overwrapped in a foil laminate pouch by purging the pouch with nitrogen and heat sealing.

Example 3

Prepare deoxygenated water having an oxygen content of less than 0.5 ppm for the formulation by degassing water, e.g., DI water, sterile water for injection, etc., with nitrogen or argon by bubbling the gas through the water until a reading of less than 0.5 ppm of $O_2$ is obtained using a dissolved oxygen meter, such as a VWR Symphony, model SP70D meter. Maintain the level of dissolved oxygen in the water during the formulation process at 0.5 or less ppm of $O_2$ by continuing to bubble inert gas through the solutions at all times including when adding the various ingredients.

Dissolve the NaCl and EDTA in the deoxygenated water, and slowly disperse the carboxymethyl cellulose into the salt solution by mixing with a propeller mixer until evenly dispersed. Place the solution in the appropriate vessel for the size of the batch and heat at 123° C. for a minimum of 30 minutes to sterilize and slowly cool to room temperature. Maintain sterility of the vessel and back fill with sterile filtered $N_2$ or Ar.

Dissolve mannitol and BAC in the deoxygenated water and adjust the pH of the solution to 5.5 with 2N NaOH prepared form the deoxygenated water. Sterile filter this solution into the sterilized formulation using $N_2$. In an opaque vessel protecting from light using the deoxygenated water, dissolve mycophenolic acid, sodium thiosulfate, and octoxynol, and adjust the pH to 7.9 with 2N NaOH. Sterile filter this solution in the formulation while maintaining a $N_2$ headspace over the formulation. Adjust the pH of the formulation to 7.8 using 2N NaOH while maintaining the nitrogen headspace/sterility.

The formulation is then sterile filtered into multi-dose bottles which have been sterilized by Co-60 irradiation by purging the empty bottle with $N_2$ before filling and filling with the formulation leaving nitrogen headspace in the filled bottle. The bottle is then overwrapped with a foil laminate pouch by purging the pouch with nitrogen and heat sealing.

Example 4

Prepare deoxygenated water having an oxygen content of less than 0.5 ppm for the formulation by degassing water, e.g., DI water, sterile water for injection, etc., with nitrogen or argon by bubbling the gas through the water until a reading of less than 0.5 ppm of $O_2$ is obtained using a dissolved oxygen meter, such as a VWR Symphony, model SP70D meter. Maintain the level of dissolved oxygen in the water during the formulation process at 0.5 or less ppm of $O_2$ by continuing to bubble inert gas through the solutions at all times including when adding the various ingredients.

Dissolve the NaCl and EDTA in the deoxygenated water, and slowly disperse the carboxymethyl cellulose into the salt solution by mixing with a propeller mixer until evenly dispersed. Place the solution in the appropriate vessel for the size of the batch and heat at 123° C. for a minimum of 30 minutes to sterilize and slowly cool to room temperature. Maintain sterility of the vessel and back fill with sterile filtered N2 or Ar.

Dissolve mannitol and citrate buffer in the deoxygenated water and adjust the pH of the solution to 5.5 with 2N NaOH prepared from the deoxygenated water. Sterile filter this solution into the sterilized formulation using $N_2$. In an opaque vessel protecting from light using the deoxygenated water, dissolve mycophenolic acid and poloxamer, and adjust the pH to 7.9 with 2N NaOH. Sterile filter this solution in the formulation while maintaining a $N_2$ headspace. Adjust the pH of the formulation to 7.8 using 2N NaOH while maintaining the nitrogen headspace/sterility.

The formulation is then sterile filtered into $N_2$ purged unit dose containers produced on a blow fill seal line. The unit dose containers are then overwrapped in a foil laminate pouch by purging the pouch with nitrogen and heat sealing.

Formulations of Mycophenolic Acid with Different Buffer Systems

Tables 2A and 2B show representative formulations of mycophenolic acid with various buffer systems which can be prepared by the following representative examples.

TABLE 2A

| | Formulation | | | | | | |
|---|---|---|---|---|---|---|---|
| Component | 1 % | 2 % | 3 % | 4 % | 5 % | 6 % | 7 % |
| Mycophenolic acid | 0.1 | 0.1 | 0.1 | 0.1 | 0.1 | 0.25 | 0.25 |
| Citric Acid | — | — | 0.2 | — | — | 0.2 | 0.2 |
| Sodium citrate | — | — | 0.14 | — | — | 0.14 | 0.14 |
| Sodium Chloride | 0.45 | 0.45 | 0.6 | 0.45 | 0.45 | 0.45 | 0.45 |
| Mannitol | 1.0 | 1.0 | 1.0 | 1.0 | 1.0 | 1.0 | 1.0 |
| Sodium Phosphate monobasic monohydrate | 0.03 | 0.03 | | 0.03 | 0.03 | — | — |
| Sodium Phosphate dibasic anhydrous | 0.25 | 0.25 | | 0.25 | 0.25 | — | — |
| EDTA | 0.1 | 0.1 | 0.1 | 0.1 | 0.1 | 0.1 | — |
| Poloxamer 407 | — | 0.2 | — | — | 0.2 | 0.2 | — |
| Octoxynol 40 (70%) | 0.02 | | 0.02 | 0.02 | | 0.02 | — |
| Sodium Thiosulfate | 0.3 | 0.3 | | 0.3 | 0.3 | — | — |
| Benzalkonium Chloride | 0.003 | — | 0.003 | 0.003 | | 0.003 | — |
| Sodium Hydroxide | qs to 7.4 | qs to 7.4 | qs to 7.4 | qs to 7.4 | qs to 7.4 | qs to 7.4 | qs to 7.4 |
| Water | qs to 100% | qs to 100% | qs to 100% | qs to 100% | qs to 100% | qs to 100% | qs to 100% |

TABLE 2B

| | Formulation | | | | | |
|---|---|---|---|---|---|---|
| Component | 8 % | 9 % | 10 % | 11 % | 12 % | 13 % |
| Mycophenolic acid | 0.25 | 0.25 | 0.5 | 0.5 | 0.5 | 0.5 |
| Citric Acid | 0.2 | 0.2 | 0.2 | — | — | 0.2 |
| Sodium citrate | 0.14 | 0.14 | 0.14 | — | — | 0.14 |
| Sodium Chloride | 0.45 | 0.45 | 0.45 | 0.45 | 0.45 | 0.45 |
| Mannitol | 1.0 | 1.0 | 1.0 | 1.0 | 1.0 | 1.0 |
| Sodium Phosphate monobasic monohydrate | — | — | — | 0.03 | 0.03 | — |
| Sodium Phosphate dibasic anhydrous | — | — | — | 0.25 | 0.25 | — |
| EDTA | — | — | — | 0.1 | 0.1 | 0.1 |
| Poloxamer 407 | — | 0.2 | — | — | -0.2 | 0.2 |
| Octoxynol 40 (70%) | 0.02 | — | 0.02 | 0.02 | — | — |
| Sodium Thiosulfate | — | — | — | 0.3 | 0.3 | — |
| Benzalkonium Chloride | 0.003 | — | — | 0.003 | — | — |
| Sodium Hydroxide | qs to 7.4 | qs to 7.8 | qs to 7.8 | qs to 7.8 | qs to 7.8 | qs to 7.8 |
| Water | qs to 100% | qs to 100% | qs to 100% | qs to 100% | qs to 100% | qs to 100% |

The formulations in Tables 2A and 2B can be prepared according to the following representative examples:

Example 5

Prepare deoxygenated water having an oxygen content of less than 0.5 ppm for the formulation by degassing water, e.g., DI water, sterile water for injection, etc., with nitrogen or argon by bubbling the gas through the water until a reading of less than 0.5 ppm of $O_2$ is obtained using a dissolved oxygen meter, such as a VWR Symphony, model SP70D meter. Maintain the level of dissolved oxygen in the water during the formulation process at 0.5 or less ppm of $O_2$ by continuing to bubble inert gas through the solutions at all times including when adding the various ingredients.

Dissolve the NaCl and EDTA in the deoxygenated water. Separately, dissolve mannitol, phosphate buffer, and BAC in the deoxygenated water and adjust the pH of the solution to 5.5 with 2N NaOH prepared form the deoxygenated water and combine with the NaCl and EDTA solution. In an opaque vessel protecting from light using the deoxygenated water, dissolve mycophenolic acid, sodium thiosulfate, and octoxynol, and adjust the pH to 7.9 with 2N NaOH. Combine with the previous solution and adjust the pH of the formulation to 7.8 using 2N NaOH while maintaining the nitrogen headspace.

The formulation is then sterile filtered into multi-dose bottles, which have been sterilized by Co-60 irradiation, by purging the empty bottle with $N_2$ before filling and filling with the formulation leaving nitrogen headspace in the filled bottle. The bottle is then overwrapped with a foil laminate pouch by purging the pouch with nitrogen and heat sealing.

Example 6

Prepare deoxygenated water having an oxygen content of less than 0.5 ppm for the formulation by degassing water, e.g., DI water, sterile water for injection, etc., with nitrogen or argon by bubbling the gas through the water until a reading of less than 0.5 ppm of $O_2$ is obtained using a dissolved oxygen meter, such as a VWR Symphony, model SP70D meter. Maintain the level of dissolved oxygen in the water during the formulation process at 0.5 or less ppm of $O_2$ by continuing to bubble inert gas through the solutions at all times including when adding the various ingredients.

Dissolve the NaCl and EDTA in the deoxygenated water. Separately, dissolve mannitol, citrate buffer, and BAC in the deoxygenated water and adjust the pH of the solution to 5.5 with 2N NaOH prepared form low $O_2$ water and combine with the formulation in step 1. In an opaque vessel protecting from light using the deoxygenated water, dissolve mycophenolic acid, sodium thiosulfate, and poloxamer, and adjust the pH to 7.9 with 2N NaOH. Combine with the previous solution and adjust the pH of the formulation to 7.8 using 2N NaOH while maintaining the nitrogen headspace.

The formulation is then sterile filtered into multi-dose bottles, which have been sterilized by Co-60 irradiation, by purging the empty bottle with $N_2$ before filling and filling with the formulation leaving nitrogen headspace in the filled bottle. The bottle is then overwrapped with a foil laminate pouch by purging the pouch with nitrogen and heat sealing.

Example 7

Prepare deoxygenated water having an oxygen content of less than 0.5 ppm for the formulation by degassing water, e.g., DI water, sterile water for injection, etc., with nitrogen or argon by bubbling the gas through the water until a reading of less than 0.5 ppm of $O_2$ is obtained using a dissolved oxygen meter, such as a VWR Symphony, model SP70D meter. Maintain the level of dissolved oxygen in the water during the formulation process at 0.5 or less ppm of $O_2$ by continuing to bubble inert gas through the solutions at all times including when adding the various ingredients.

Dissolve the NaCl and EDTA in the deoxygenated water. Separately, dissolve mannitol and citrate buffer in the deoxygenated water and adjust the pH of the solution to 5.5 with 2N NaOH prepared form the deoxygenated water and combine with the formulation in step 1. In an opaque vessel protecting from light using low $O_2$ water, dissolve mycophenolic acid and poloxamer, and adjust the pH to 7.9 with 2N NaOH. Combine with the previous solution and adjust the pH of the formulation to 7.8 using 2N NaOH while maintaining the nitrogen headspace.

The formulation is then sterile filtered into unit-dose bottles which have been nitrogen purged on blow fill seal machine. The bottle is then overwrapped in a foil laminate pouch by purging the pouch with nitrogen and heat sealing.

Example 8

Prepare deoxygenated water having an oxygen content of less than 0.5 ppm for the formulation by degassing water, e.g., DI water, sterile water for injection, etc., with nitrogen or argon by bubbling the gas through the water until a reading of less than 0.5 ppm of $O_2$ is obtained using a dissolved oxygen meter, such as a VWR Symphony, model SP70D meter. Maintain the level of dissolved oxygen in the water during the formulation process at 0.5 or less ppm of $O_2$ by continuing to bubble inert gas through the solutions at all times including when adding the various ingredients.

Dissolve the NaCl and EDTA in the deoxygenated water. Separately, dissolve the mannitol and phosphate buffer in the deoxygenated water and adjust the pH of the solution to 5.5 with 2N NaOH prepared form low $O_2$ water and combine with the formulation in previous step. In an opaque vessel protecting from light using the deoxygenated water, dissolve mycophenolic acid, sodium thiosulfate and poloxamer, and adjust the pH to 7.9 with 2N NaOH. Combine with the previous solution and adjust the pH of the formulation to 7.8 using 2N NaOH while maintaining the nitrogen headspace.

The formulation is then sterile filtered into unit-dose bottles which have been nitrogen purged using a blow fill seal. The bottle is then overwrapped in a foil laminate pouch by purging the pouch with nitrogen and heat sealing.

Additional Formulations of Mycophenolic Acid with Polycarbophil and Chitosan

Tables 3A and 3B show representative formulations of mycophenolic acid with polycarbophil and chitosan which can be prepared by the following representative example.

TABLE 3A

| | Formulation | | | | | |
|---|---|---|---|---|---|---|
| Component | 1 % | 2 % | 3 % | 4 % | 5 % | 6 % |
| Mycophenolic acid | 0.1 | 0.1 | 0.1 | 0.1 | 0.25 | 0.25 |
| Citric Acid | — | — | 0.2 | 0.2 | — | — |
| Sodium citrate | — | — | 0.14 | 0.14 | — | — |
| Sodium Chloride | 0.5 | 0.5 | 0.5 | 0.5 | 0.45 | 0.45 |
| Mannitol | 1.0 | 1.0 | 1.0 | 1.0 | 0.5 | 0.5 |
| Polycarbophil | 0.9 | 0.9 | 0.9 | 0.9 | 0.9 | 0.9 |
| Chitopharm-L | 0.025 | 0.025 | 0.025 | 0.025 | 0.035 | 0.035 |
| HCl | 1.5 | 1.5 | 1.5 | 1.5 | 1.5 | 1.5 |
| EDTA | 0.1 | 0.1 | 0.1 | 0.1 | 0.1 | 0.1 |
| Poloxamer 407 | — | 0.2 | — | 0.2 | — | 0.2 |
| Octoxynol 40 (70%) | 0.02 | — | 0.02 | — | 0.02 | — |
| Sodium Thiosulfate | 0.3 | 0.3 | — | — | 0.3 | 0.3 |
| Benzalkonium Chloride | 0.003 | — | 0.003 | — | 0.003 | — |
| Sodium Hydroxide | qs to 7.4 | qs to 7.4 | qs to 7.4 | qs to 7.4 | qs to 7.4 | qs to 7.4 |
| Water | qs to 100% | qs to 100% | qs to 100% | qs to 100% | qs to 100% | qs to 100% |

TABLE 3B

| | Formulation | | | | | |
|---|---|---|---|---|---|---|
| Component | 7 % | 8 % | 9 % | 10 % | 11 % | 12 % |
| Mycophenolic acid | 0.25 | 0.25 | 0.5 | 0.5 | 0.5 | 0.5 |
| Citric Acid | 0.2 | 0.2 | — | — | 0.2 | 0.2 |
| Sodium citrate | 0.14 | 0.14 | — | — | 0.14 | 0.14 |
| Sodium Chloride | 0.45 | 0.45 | 0.4 | 0.4 | 0.4 | 0.4 |
| Mannitol | 0.5 | 0.5 | 0.15 | 0.15 | 0.15 | 0.15 |
| Polycarbophil | 0.9 | 0.9 | 0.9 | 0.9 | 0.9 | 0.9 |
| Chitopharm-L | 0.035 | 0.035 | 0.05 | 0.05 | 0.05 | 0.05 |
| HCl | 1.5 | 1.5 | 1.5 | 1.5 | 1.5 | 1.5 |
| EDTA | 0.1 | 0.1 | 0.1 | 0.1 | 0.1 | 0.1 |
| Poloxamer 407 (70%) | — | 0.2 | — | 0.2 | — | 0.2 |
| Octoxynol 40 | 0.02 | — | 0.02 | — | 0.02 | — |
| Sodium Thiosulfate | — | — | 0.3 | 0.3 | — | — |
| Benzalkonium Chloride | 0.003 | — | 0.003 | — | 0.003 | — |
| Sodium Hydroxide | qs to 7.4 | qs to 7.8 | qs to 7.8 | qs to 7.8 | qs to 7.8 | qs to 7.8 |
| Water | qs to 100% | qs to 100% | qs to 100% | qs to 100% | qs to 100% | qs to 100% |

Example 9

Prepare deoxygenated water having an oxygen content of less than 0.5 ppm for the formulation by degassing water, e.g., DI water, sterile water for injection, etc., with nitrogen or argon by bubbling the gas through the water until a reading of less than 0.5 ppm of $O_2$ is obtained using a dissolved oxygen meter DO meter VWR Symphony, model SP70D []. Maintain the level of dissolved oxygen in the water during the formulation process at 0.5 or less ppm of $O_2$ by continuing to bubble inert gas through the solutions at all times.

Dissolve 50% of the NaCl with EDTA in the deoxygenated water, and slowly disperse the polycarbophil into the salt solution by mixing with a propeller mixer until evenly dispersed. Place the solution in the appropriate vessel for the size of the batch and heat at 123° C. for a minimum of 30 minutes to sterilize and slowly cool to room temperature. Maintain sterility of the vessel and back fill with sterile filtered $N_2$ or Argon.

Dissolve the HCl with the remainder of the NaCl and 50% of the surfactant (poloxamer or octoxynol) in the deoxygenated water. Slowly, dissolve the chitosan in this solution while continuing to bubble $N_2$ through the solution. Sterile filter the chitosan solution into the polycarbophil formulation while continually mixing while keeping under a $N_2$ blanket.

Dissolve mannitol, citrate buffer (if present), BAC in the deoxygenated water and adjust the pH of the solution to 5.5 with 2N NaOH prepared form low $O_2$ water. Sterile filter this solution into the sterilized formulation using $N_2$. In an opaque vessel protecting from light using low $O_2$ water, dissolve mycophenolic acid, remainder of surfactant (octoxynol, or poloxamer), sodium thiosulfate if present, and adjust the pH to 7.9 with 2NaOH. Sterile filter this solution in the formulation while maintaining a $N_2$ headspace over the formulation. Adjust the pH of the formulation to 7.8 using 2N NaOH while maintaining the nitrogen headspace/sterility.

The formulation is then filled into multi-dose bottles which have been sterilized by Co-60 irradiation or unit dose containers by purging the empty bottle/containers with $N_2$ before filling and filling with the formulation leaving nitrogen headspace in the filled bottle/containers. The bottle or unit dose containers are overwrapped with a foil laminate pouch by purging the pouch with nitrogen and heat sealing.

Formulations of Mycophenolic Acid for Injection

The following table provides prophetic formulations of mycophenolic acid for intraocular injection. In preparing such formulations, it is preferable to degas any water used in the formulation to a dissolved oxygen content level of less than 0.5 ppm.

| Ingredient | Concentration (%) | Concentration (%) | Concentration (%) | Concentration (%) |
|---|---|---|---|---|
| Mycophenolic Acid | 0.1 | 0.1 | 0.5 | 0.1-0.5 |
| Edetate Disodium (Dihydrate) | 0.1 | 0.1 | 0.1 | 0-0.1 |
| Citric Acid (Monohydrate) | — | — | — | 0.05 |
| Monobasic Sodium Phosphate (Anydrous)* | 0.24 | 0.12 | 0.12 | — |
| Dibasic Sodium Phosphate (Anhydrous)* | 0.43 | 0.57 | 0.57 | 0.63 |
| Sodium Chloride | q.s. to isotonic | q.s. to isotonic | q.s. to isotonic | q.s. to isotonic |
| Polysorbate 80 | 0-0.015 | 0-0.015 | 0-0.015 | 0-0.015 |
| Sodium Hydroxide/ Hydrochloric Acid | Adjust pH to 7.0 | Adjust to pH 7.4 | Adjust to pH 7.4 | Adjust pH to 7.4 |
| Water for Injection | q.s. to 100% | q.s. to 100% | q.s. to 100% | q.s. to 100% |

*50 mM total buffer concentration

Only the preferred embodiment of the present invention and examples of its versatility are shown and described in the present disclosure. It is to be understood that the present invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances, procedures and arrangements described herein. Such equivalents are considered to be within the scope of this invention, and are covered by the following claims.

What is claimed is:

1. An ophthalmic formulation comprising mycophenolic acid or salt thereof as an active ingredient in an aqueous medium with a reduced level of dissolved oxygen relative to saturation level, wherein the oxygen level is less than 3 ppm, and wherein at least 90% of an initial amount of the mycophenolic acid or salt thereof as an active ingredient remains in the ophthalmic formulation after a period of at least 18 months from an initial preparation of the ophthalmic formulation.

2. The ophthalmic formulation according to claim 1, wherein the aqueous medium has oxygen level of less than 1 ppm.

3. The ophthalmic formulation according to claim 1, further comprising an alkali thiosulfate.

4. The ophthalmic formulation according to claim 1, further comprising one or more additional ingredients selected from an ophthalmically acceptable vehicle, viscosity modifier, buffer, osmolality adjusting agent, pH adjusting agent, antioxidant, chelating agent, preservative, or wetting agent.

5. The ophthalmic formulation according to claim 1, packaged in an opaque container or pouch including a metal foil for reducing oxygen permeability through the container or pouch.

6. The ophthalmic formulation according to claim 1, further comprising polycarbophil and optionally chitosan.

7. A method of treating a subject having an eye disease, the method comprising administering to an eye of a subject in need thereof the ophthalmic formulation of claim 1.

8. The method according to claim 7, wherein the ophthalmic formulation is administered by injecting the ophthalmic formulation into the eye of the subject.

9. The method according to claim 7, wherein the eye disease is dry eye.

10. An ophthalmic formulation comprising mycophenolic acid or salt thereof as an active ingredient and an alkali thiosulfate in an aqueous medium with a reduced level of dissolved oxygen relative to saturation level; wherein the oxygen level is less than 3 ppm.

11. The ophthalmic formulation according to claim 10, wherein the alkali thiosulfate is sodium thiosulfate.

12. The ophthalmic formulation according to claim 10, further comprising one or more additional ingredients selected from an ophthalmically acceptable vehicle, viscosity modifier, buffer, osmolality adjusting agent, pH adjusting agent, antioxidant, chelating agent, preservative, or wetting agent.

13. The ophthalmic formulation according to claim 10, packaged in an opaque container or pouch including a metal foil for reducing oxygen permeability through the container or pouch.

14. The ophthalmic formulation according to claim 10, wherein the formulation has a pH of greater than 7.0.

* * * * *